US010426344B2

(12) United States Patent
Konno et al.

(10) Patent No.: US 10,426,344 B2
(45) Date of Patent: Oct. 1, 2019

(54) MEDICAL SERVICE SUPPORT DEVICE, MEDICAL SERVICE SUPPORT SYSTEM AND MEDICAL SERVICE SUPPORT METHOD

(71) Applicant: NIHON KOHDEN CORPORATION, Tokorozawa (JP)

(72) Inventors: Norihito Konno, Tokyo (JP); Hirokazu Ogino, Tokyo (JP); Fumiyuki Matsumura, Tokyo (JP); Hirohiko Ikeya, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 15/975,332

(22) Filed: May 9, 2018

(65) Prior Publication Data

US 2018/0338683 A1 Nov. 29, 2018

(30) Foreign Application Priority Data

May 24, 2017 (JP) ................................. 2017-103081

(51) Int. Cl.
| | |
|---|---|
| A61B 5/00 | (2006.01) |
| A61B 5/11 | (2006.01) |
| G16H 10/60 | (2018.01) |
| G16H 80/00 | (2018.01) |
| A61B 5/0478 | (2006.01) |

(Continued)

(52) U.S. Cl.
CPC .......... *A61B 5/0024* (2013.01); *A61B 5/0402* (2013.01); *A61B 5/0478* (2013.01); *A61B 5/11* (2013.01); *A61B 5/4809* (2013.01); *A61B 5/4812* (2013.01); *A61B 5/7465* (2013.01); *A61B 5/01* (2013.01); *A61B 5/082* (2013.01); (Continued)

(58) Field of Classification Search
None
See application file for complete search history.

(56) References Cited

U.S. PATENT DOCUMENTS

| | | | | |
|---|---|---|---|---|
| 2005/0115561 A1* | 6/2005 | Stahmann | ............ | A61B 5/0031 128/200.24 |
| 2006/0200011 A1* | 9/2006 | Suzuki | ................. | A61B 5/0205 600/301 |

(Continued)

FOREIGN PATENT DOCUMENTS

JP 2013208253 A 10/2013

*Primary Examiner* — Muhammad N Edun
*Assistant Examiner* — Jerold B Murphy
(74) *Attorney, Agent, or Firm* — Dorsey & Whitney LLP

(57) ABSTRACT

To provide a medical service support device, a medical service support method and a medical service support system capable of properly watching patients in accordance with states of the patients. A medical service support device includes an electrocardiogram sensor attached to a patient and measuring electrocardiogram data of the patient, an analysis unit analyzing the electrocardiogram data, an acceleration sensor detecting a motion of the patient, and an attention calling unit transmitting attention calling information and patient identification information for specifying the patient toward the external portion of the device when it is determined that the patient is in a REM sleep state based on an analysis result by the analysis unit as well as determined that the patient has moved to a given state based on a detection result by the acceleration sensor.

8 Claims, 4 Drawing Sheets

(51) Int. Cl.
*A61B 5/0402* (2006.01)
*A61B 5/01* (2006.01)
*A61B 5/08* (2006.01)
*A61B 5/145* (2006.01)

(52) U.S. Cl.
CPC .......... *A61B 5/14542* (2013.01); *G16H 10/60* (2018.01); *G16H 80/00* (2018.01)

(56) References Cited

U.S. PATENT DOCUMENTS

| | | | |
|---|---|---|---|
| 2015/0026647 A1* | 1/2015 | Park | G06F 3/0488 715/863 |
| 2015/0150498 A1* | 6/2015 | George | A61B 5/4818 600/301 |
| 2015/0164682 A1* | 6/2015 | Remmers | A61B 5/4812 600/301 |
| 2016/0015314 A1* | 1/2016 | Dusanter | A61B 5/4812 600/301 |

* cited by examiner

MEDICAL SERVICE SUPPORT DEVICE, MEDICAL SERVICE SUPPORT SYSTEM AND MEDICAL SERVICE SUPPORT METHOD

CROSS REFERENCE TO RELATED APPLICATION

This application claims priority to JP Application No. JP 2017-103081 filed May 24, 2017 which is incorporated herein by reference, in its entirety, for any purpose.

FIELD

The present disclosure relates to a medical service support device, a medical service support system and a medical service support method.

BACKGROUND

In a hospital accommodating patients, an in-hospital informing system using medical equipment generating a nurse call or an alarm is used as a system for informing a medical worker of a patient requiring emergency treatment (JP-A-2013-208253 (Patent Literature 1).

However, for example, a patient who may fall from a bed in a REM sleep state does not require emergency treatment but should be watched with care.

In order to watch the patient who may fall from the bed, it is effective to watch the patient so as to correspond to a sleep state by specifying whether the sleep state of the patient is REM sleep or Non-REM sleep. Here, the specification of the sleep state can be determined by an electroencephalograph using multi-channel electrodes and by measuring brain waves using a paste for reducing noise.

However, the electroencephalograph using multi-channel electrodes or the electroencephalograph using the paste for reducing noise is a heavy burden for the patient, and the measurement is also a heavy burden for the medical worker performing measurement.

SUMMARY

Accordingly, an object of the present disclosure may be to provide a medical service support device, a medical service support system and a medical service support method capable of easily determining a patient who should be watched with care and informing the medical worker of the patient.

A medical service support device according to the present disclosure may include a measurement unit attached to a patient and including at least one sensor that measures biological information of the patient, an analysis unit analyzing the biological information, a detection unit detecting a motion of the patient and an attention calling unit transmitting attention calling information and patient identification information for specifying the patient toward the external portion of the device when it is determined that the patient is in a REM sleep state based on an analysis result by the analysis unit as well as determined that the patient has moved to a given state based on a detection result by the detection unit.

According to the above configuration, the attention calling unit transmits attention calling information by easily determining the patient to whom attention should be paid based on a fact that the patient is in the REM sleep state and has moved to the given state, therefore, the medical worker can specify the patient to be watched with care among a large number of patients.

A medical service support system according to the present disclosure may include the medical service support device and an emergency informing unit informing the contents of emergency treatment by detecting that the emergency treatment is necessary for the patient.

According to the above configuration, the attention calling unit transmits attention calling information by easily determining the patient to whom attention should be paid based on the fact that the patient is in the REM sleep state and has moved to the given state, therefore, the medical worker can specify the patient to be watched with care among a large number of patients. Separately from the specification of the patient who should be watched with care, when emergency treatment is necessary for the patient, the patient can be positively specified and nursed in accordance with information from the emergency informing unit. That is, a proper response can be made in accordance with the state of the patient.

A medical service support method according to the present disclosure may include the steps of measuring biological information of a patient, analyzing the biological information, determining whether the patient is in a REM sleep state or not based on an analysis result in the step of analysis, detecting a motion of the patient by a detection unit, determining whether the motion of the patient detected by the detection unit is movement to a given state or not, and transmitting attention calling information and patient identification information for specifying the patient to the external portion of the device when it is determined that the patient is in the REM sleep state as well as determined that the patient has moved to the given state.

According to the above method, when it is determined that the patient is in the REM sleep state as well as determined that the patient has moved to the given state, the patient to whom attention should be paid is easily determined based on the determination and attention calling information is transmitted, therefore, the medical worker can specify the patient to be watched with care among a large number of patients.

According to the present disclosure, it is possible to easily determine the patient who should be watched with care and to inform the medical worker of the patient.

DETAILED DESCRIPTION

Hereinafter, a medical service support device, a medical service support system and a medical service support method according to embodiments of the present disclosure will be explained with reference to the drawings. The present disclosure relates to a medical service support device, a medical service support method and a medical service support system including the medical service support device capable of properly watching patients in accordance with states of the patients by easily determining whether a patient is in a REM sleep state or a Non-REM sleep state without using an electroencephalograph by multi-channel electrodes or an electroencephalograph by a paste for reducing noise as well as determining operations concerning whether the patient has moved to a given state or the like.

<First Embodiment>

Figure 1:
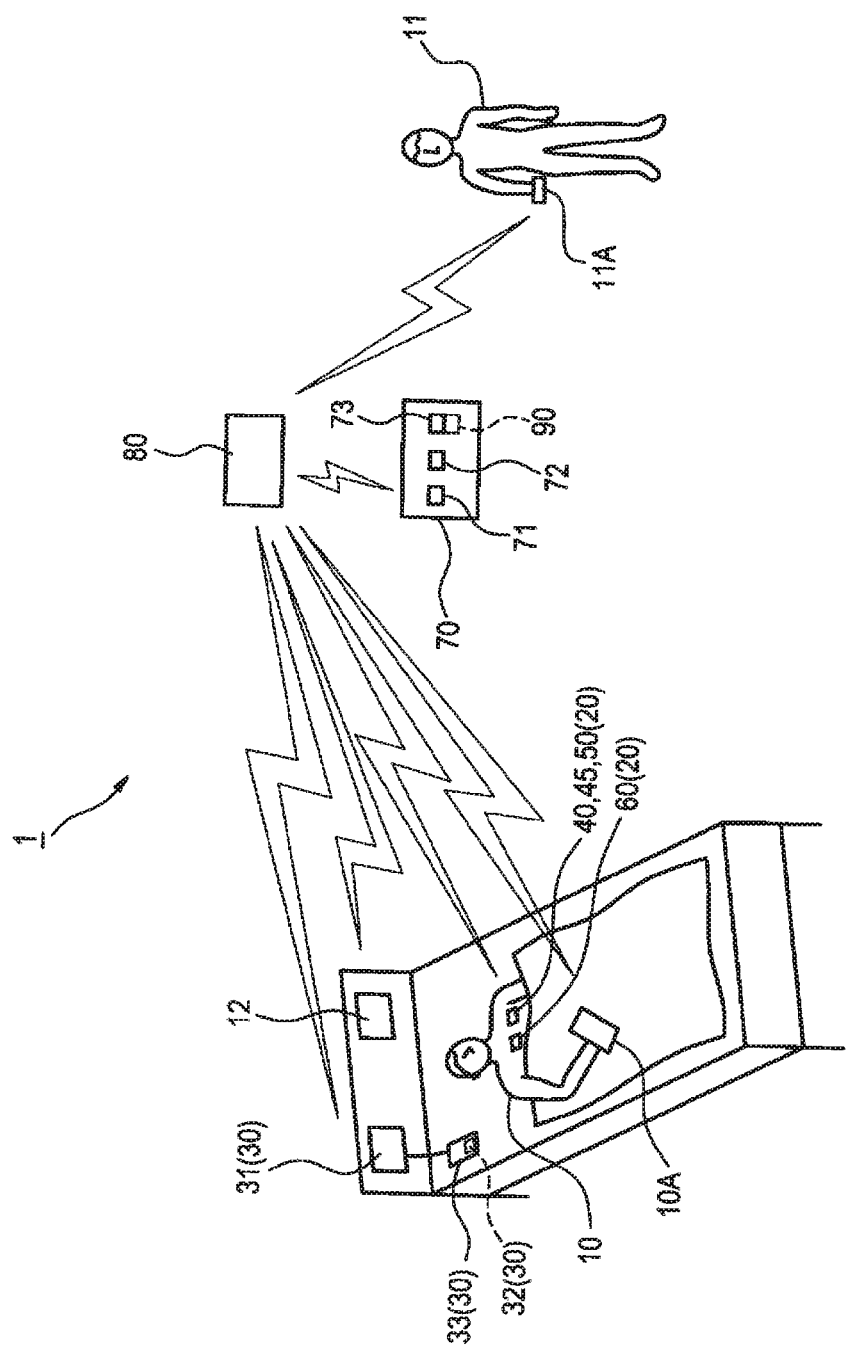
FIG. 1 is an explanatory view showing an outline of a medical service support device and a medical service support system according to an embodiment of the present disclosure.

As shown in FIG. 1, a medical service support system 1 according to an embodiment may include a medical service support device 20 that informs a medical worker 11 of a patient 10 who should be watched with care and an emergency informing unit 30 such as a nurse call 33 that informs that emergency treatment is necessary for the patient 10.

The patient 10 who should be watched with care may be a patient to whom the medical worker 11 should pay attention previously preventing injuries and so on due to falling from a bed though there is no urgency such as informing by the emergency informing unit 30. The patient 10 who should be watched with care is, for example, the patient 10 and the like who may fall to a floor of a sickroom from a bed of the sickroom.

The medical service support system 1 may be configured by including a display apparatus 70 having display units 71 and 72. The display unit 71 is configured to display attention calling information as contents of the medical service support device 20. The display unit 72 is configured to display the emergency treatment contents as the contents of the emergency informing unit 30. Also in the medical service support system 1, a terminal apparatus 11A carried by each medical worker 11, the medical service support device 20, the emergency informing unit 30 and the display apparatus 70 are configured to communicate with one another through an access point 80 as an example of apparatus relating to communication.

<Medical Service Support Device 20>

The medical service support device 20 may be a device respectively arranged for each patient 10, including a measurement unit, an analysis unit, a detection unit and an attention calling unit. It is generally known that a REM sleep state is shallow sleep in which a brain works while a body sleeps. It is also known that a Non-REM sleep is deep sleep in which the body and the brain are resting. The medical service support device 20 is a device that determines the patient 10 who should be watched with care based on the sleep state (REM sleep state, Non-REM sleep state) and the operation of the patient 10.

Figure 2:
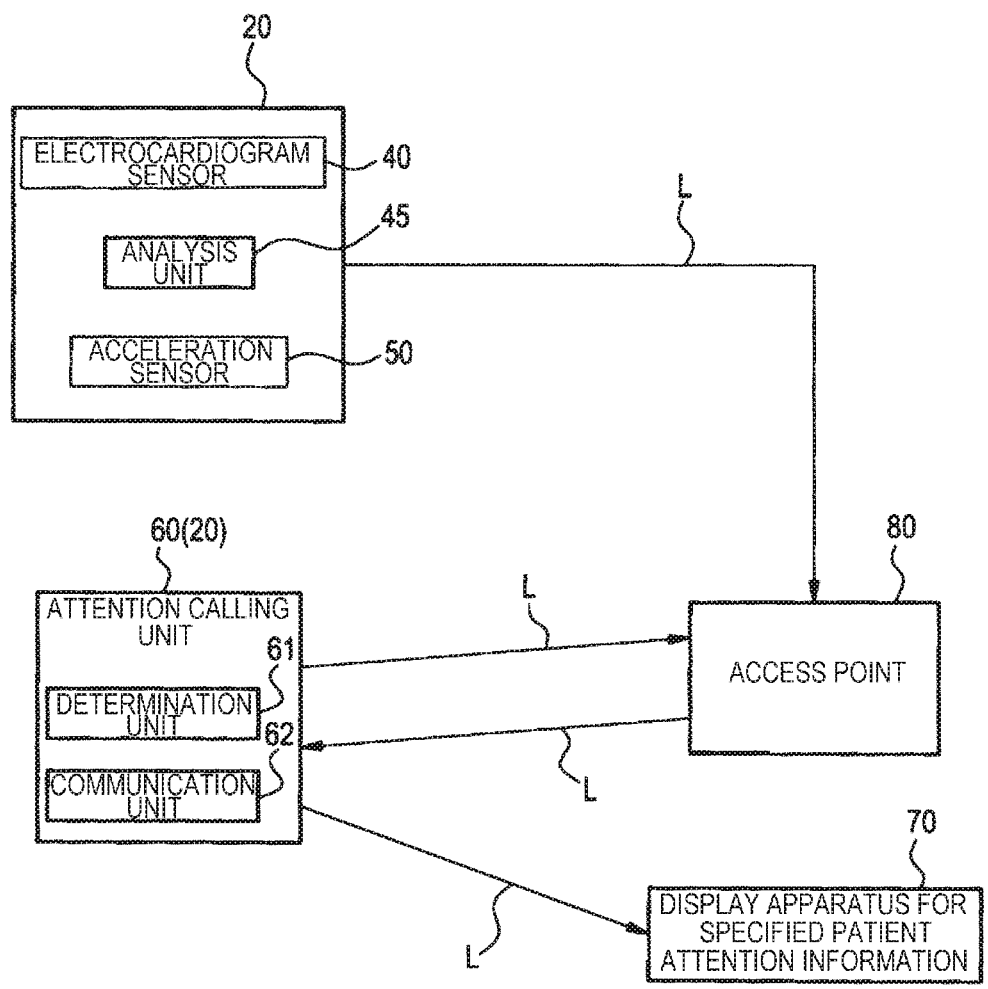
FIG. 2 is a function block diagram showing an outline of the medical service support device according to the embodiment of the present disclosure.

The medical service support device 20 shown in FIG. 1 and FIG. 2 includes an electrocardiogram sensor 40 (an example of the measurement unit), an analysis unit 45, an acceleration sensor 50 (an example of the detection unit) and an attention calling unit 60. The electrocardiogram sensor 40, the analysis unit 45, the acceleration sensor 50 and the attention calling unit 60 are configured to perform communication with one another by a communication network L that performs communication in accordance with a general-purpose protocol as shown in FIG. 2. The communication network L may be any of wired communication lines such as wired LAN (Local Area Network) and wireless communication lines such as Bluetooth (trademark), BLE (Bluetooth Low Energy) and wireless LAN (Local Area Network).

<Measurement Unit>

The measurement unit may be a sensor attached to the patient and measuring biological information of the patient. The measurement unit may be the electrocardiogram sensor 40 that measures electrocardiogram data as an example of biological information of the patient 10. FIG. 1 shows a state in which the electrocardiogram sensor 40 is attached to a chest portion of the patient 10 as an example of attachment of the electrocardiogram sensor 40. The electrocardiogram data measured by the electrocardiogram sensor 40 is transmitted to the analysis unit 45.

<Analysis Unit 45>

The analysis unit 45 may be configured to analyze biological information measured by the measurement unit. The analysis unit 45 is configured to acquire and analyze electrocardiogram data measured by the electrocardiogram sensor 40 and to determine whether the sleep state of the patient 10 is the REM sleep state or the Non-REM sleep state. The analysis unit 45 is configured to transmit a determination result obtained by determining whether the sleep state of the patient 10 is the REM sleep state or the Non-REM sleep state to the attention calling unit 60.

<Detection Unit>

The detection unit is an apparatus for detecting a motion of the patient 10. As an example, the detection unit can be formed by a three-axis acceleration sensor 50 that detects positional variation of the patient 10 in X-coordinates, Y-coordinates and Z-coordinates and detects angular variation concerning the patient 10 in any of an XY-plane, a ZY-plane and a ZX-plane. The acceleration sensor 50 can detect the positional variation and the angular variation of the patient 10 plural times to thereby determine whether there is a motion in the patient 10 based on detection results of plural times.

The acceleration sensor 50 may be configured to determine whether the patient 10 has moved to a given state or not based on the detected positional variation or angular variation of the patient. The movement to the given state means that a state in which there is a motion to be detected when the patient 10 is in imminent danger such as falling from the bed. The motion requires an attention such as a check of the state of the patient 10 though it is different from a sudden change of a condition which requires emergency treatment. As an example, a change amount of a motion in which the patient 10 may fall from the bed is calculated based on a width and a length as dimensions of the bed and a height and a body width of the patient 10, and the movement to the given state can be determined when a motion exceeding the change amount is detected by the acceleration sensor 50. The acceleration sensor 50 is configured to transmit the detection result concerning whether the patient 10 has moved to the given state or not to the attention calling unit 60.

<Attention Calling Unit 60>

The attention calling unit 60 is configured to determine whether each patient is a patient who should be watched with care or not based on the sleep state (the REM sleep state or the Non-REM sleep state) of the patient and the motion concerning whether the patient has moved to the given state and to transmit the determination result to external portion of the device. The attention calling unit 60 shown in FIG. 2 includes a determination unit 61 determining whether the patient 10 is the patient who should be watched with care and a communication unit 62 informing the medical worker 11 of information such as attention calling information of the patient 10 who should be watched with care by transmitting the information toward the external portion of the medical service support device 20.

The determination unit 61 may be configured to successively acquire the analysis result of the sleep state (the REM sleep state and the Non-REM sleep state) of the patient 10 from the analysis unit 45. The determination unit 61 is configured to successively acquire the detection result concerning whether the patient 10 has moved to the given state or not from the acceleration sensor 50. The determination unit 61 is configured to determine whether the patient 10 as a measurement target is the patient who should be watched with care or not based on the analysis result acquired from the analysis unit 45 and the detection result acquired from the acceleration sensor 50.

Whether the patient 10 as a measurement target is the patient who should be watched with care or not can be determined by at least two-stage determination. That is, the determination unit 61 determines the sleep state indicating whether the patient 10 is in the REM sleep state or in the Non-REM sleep state as determination of the first stage, and determines the motion indicating whether the patient 10 has moved to the given state or not as determination of the second stage.

Determination results concerning whether the patient 10 should be watched with care or not by the determination unit 61 are as follows:

(1) Attention Calling (Alert) is Necessary

The patient 10 moved to the given state in the REM sleep state may fall from a bed or something. Accordingly, the determination unit 61 determines that the patient 10 moved to the given state in the REM sleep state as a patient to whom attention calling (alert) is necessary to be watched with care and determines that the patient 10 should be informed to the medical worker 11.

(2) Attention is Necessary

In the motionless patient 10 though in the REM sleep state, there is a little possibility that the motion such as falling from the bed or something immediately occurs, therefore, the determination unit 61 determines that it is not necessary to inform the medical worker 11 of that state. It is known that the patient 10 may unconsciously move his/her body in the REM sleep state even when there is no motion and posture change in the patient 10, and there is a possibility that the patient 10 in the REM sleep state moves to the given state, therefore, it is determined that attention equivalent to the attention calling is necessary.

(3) Light Attention is Necessary

In a case where the patient 10 is in the Non-REM sleep state as well as there is a motion smaller than the motion in the given state in the patient 10, the determination unit 61 determines that light attention is necessary. Whether there is a motion smaller than the motion in the given state or not in the patient 10 can be determined by determining whether there is the change amount of the motion in which the patient may fall from the bed or the like though a degree of attention is lower than the patient 10 requiring attention calling, and can be decided based on medical conditions, environment and so on of the patient 10.

(4) None of Attention Calling, Attention and Light Attention is not Necessary

The motionless patient 10 in the Non-REM sleep state seldom moves his/her body unconsciously, and there is no possibility of falling from the bed and the like, therefore, the determination unit 61 determines that the state does not require any of attention calling, attention and light attention.

Furthermore, when the determination unit 61 determines that the patient 10 requires attention calling (alert) who has moved to the given state in the REM sleep state, the determination unit 61 creates attention calling information indicating that the patient 10 is the patient to whom attention should be paid.

The attention calling information can be various types of displays and states for alerting the medical worker 11. As an example, the attention calling information may be information concerning the patient, may be character information indicating states to which attention should be paid such as "Attention of falling from bed" and may be character information concerning a detection result such as "detection of large motion". The attention calling information may also be instruction contents with respect to the medical worker 11, which is, for example, character information indicating "Please patrol just in case". The attention calling information may further be issued by vibrating a portable terminal of the medical worker 11 in addition to character information, and may be informed by blinking a light emission part of the portable terminal.

The determination unit 61 may be configured to acquire patient identification information for specifying the patient for whom attention calling information has been created. The patient identification information includes, for example, a patient ID individually set for the patient 10, an identification number of a hospital bed used by the patient 10 and the like as examples. The patient identification information is held in an apparatus from which the attention calling unit 60 can acquire information. The patient identification information may be held in any of the electrocardiogram sensor 40, a terminal apparatus 10A of the patient, a bedside monitor 12 installed in a bed of the patient 10 and the emergency informing unit 30, and may be held inside the attention calling unit 60 and acquired by the determination unit 61.

The attention calling information (alert) and the patient identification information are informed from the attention calling unit 60 to the medical worker 11. The notification between the attention calling unit 60 and the medical worker 11 may be performed by using a network such as the communication network L communication of which is performed in accordance with the general-purpose protocol from the communication unit 62 shown in FIG. 2 and may be performed through the apparatus such as the access point 80 shown in FIG. 2.

The attention calling information and the patient identification number transmitted to the apparatus which can be checked by the medical worker 11 may be displayed on the display unit 71 of the display apparatus 70 shown in FIG. 1 and may be displayed on the terminal apparatus 11A carried by the medical worker 11.

<Emergency Informing Unit 30>

The emergency informing unit 30 of the emergency support system 1 includes a detection unit 31 detecting that emergency treatment is necessary for the patient 10 and a communication unit 32 transmitting a detection result of the detection unit 31 to the external portion of the emergency informing portion 30 as shown in FIG. 1.

The detection unit 31 may be an electrocardiograph that detects a sudden change of the condition of the patient 10. The electrocardiograph 31 can be configured to include the nurse call 33 for informing the sudden change of the patient 10 by an attendant.

The communication unit 32 is installed in the bed of the patient 10 and can perform communication by using the nurse call 33 in which Bluetooth (trademark) is built in. The contents of emergency treatment transmitted from the electrocardiograph 31 of the emergency informing unit 30 is received by an apparatus capable of being checked by the medical worker 11 such as the display unit 72 and the terminal apparatus 11A of the medical worker 11. The informing by the display unit 72 may be performed by displaying characters such as "condition changes suddenly" or the like on the display unit 72, by generating a notification sound from a speaker (not shown) of the display unit 72 and by blinking a lamp (not shown) of the display apparatus 70.

The emergency informing unit 30 may be a system that notifies the contents of emergency treatment to the display apparatus when detecting that the patient 10 requires emergency treatment, and various types of systems such as the nurse call 33 which have been hitherto used can be used.

Next, an operation example 1 and an operation example 2 of a medical service support method in the above configuration will be explained with reference to FIG. 1 to FIG. 3.

<Operation Example 1>

An operation example of the medical service support method using the medical service support device 20 will be explained as an operation example 1.

An apparatus in which the electrocardiogram sensor 40, the analysis unit 45 and the acceleration sensor 50 are integrated is attached to each of plural patients 10. The attention calling unit 60 is attached to a chest portion of the patient 10, which is closed to the electrocardiogram sensor 40 shown in FIG. 1 (S1, start of watching).

The electrocardiogram sensor 40 measures an electrocardiogram of the patient 10 (S2, measurement step) and transmits the measured electrocardiogram data to the analysis unit 45.

The analysis unit 45 analyzes the received electrocardiogram data and analyzes the sleep state of the patient 10 (S3, analysis step). The analysis unit 45 determines whether the sleep state of the patient 10 as the measurement target is REM sleep or Non-REM sleep based on the analysis result of the electrocardiogram data (S4, sleep-state determination step). In the example, the analysis unit 45 determines that the patient 10 is in the REM sleep state (YES in S4), and transmits the determination result to the attention calling unit 60. The determination unit 61 of the attention calling unit 60 acquires the determination result that the patient 10 is in the REM sleep state from the analysis unit 45.

The acceleration sensor 50 detects positional variation and angular variation of the patient 10 plural times (S5, detection step). The acceleration sensor 50 determines that the patient has moved to the given state or not from detection results of positional variation and angular variation of the patient 10 (S6, motion determination step). The acceleration sensor 50 transmits the determination result to the attention calling unit 60.

When the patient 10 has moved to the given state (YES in S6), the determination unit 61 determines that the patient 10 is a patient to whom attention should be paid and attention calling is necessary. The determination unit 61 creates attention calling information of the patient 10 and acquires patient identification information for specifying the patient 10 for whom the attention calling information has been created. The determination unit 61 transmits attention calling information and a patient identification number to an apparatus which can be checked by the medical worker 11 such as the display unit 71 (S7, attention calling information notification step). The medical worker 11 checks the attention calling information and the patient identification number displayed on the display unit 71, thereby making a response corresponding to the notification contents of the determination unit 61 and performs appropriate treatment to the patient 10. When an operation of ending the watching is not performed, the watching of the patient 10 is continued (YES in S12), and when an operation of ending the watching is performed (No in S12), the watching ends (S13).

According to the above configuration, the patient 10 in the REM sleep state as well as moved in the given state is determined as the patient to whom attention should be paid and attention calling is necessary, and attention calling information and the patient identification number of the patient 10 are transmitted to the external portion, therefore, the medical worker 11 can specify the patient 10 who should be watched with care such as the patient having the possibility of falling from the bed among many patients 10.

When the patient 10 has not moved to the given state in S6 (No in S6), the determination unit 61 determines that attention equivalent to attention calling is necessary though the attention calling (alert) is not necessary (S8).

According to the configuration, the patient 10 in the REM sleep state having a possibility of moving though attention calling (alert) is not necessary can be specified and the sleep state and presence of a motion of the patient 10 can be continuously determined, therefore, it is possible to properly watch the patient 10.

When it is determined that the sleep state of the patient 10 is the Non-REM sleep in S4 (No in S4), the acceleration sensor 50 detects a motion of the patient 10 (S9, detection step).

The determination unit 61 acquires a determination result concerning whether there is a motion in the patient 10 or not even though the motion is smaller than the motion of the given state from the acceleration sensor 50.

When there is a motion in the patient 10 though the motion is smaller than the motion of the given state (YES in S10), it is determined that light attention calling is necessary for the patient 10 (S11).

According to the above configuration, the patient 10 with a large motion can be specified among the patients 10 in the Non-REM sleep state who are generally considered not to move their body unconsciously, therefore, it is possible to properly watch the patient 10 so that falling from the bed or something does not occur.

When there is no motion of the patient 10 in S10, the determination unit 61 determines that attention calling with respect to the patient 10 as the measurement target is not necessary (NO in S10), and the process returns to the determination of the sleep state (S4).

According to the above structure, even in the case where the motion is not detected in the Non-REM sleep state in which bodies generally do not move unconsciously, many patients 10 can be properly watched by continuously watching the patients 10.

As explained above, it is possible to determine that the patient 10 is in the REM sleep state with a simple method according to the configuration of the present disclosure. Furthermore, the patient to be watched with care is easily determined by combining the determination of the sleep state of the patient 10 and the determination of the motion in the given state of the patient 10, and the attention calling unit 60 transmits attention calling information, therefore, the medical worker 11 can specify the patient 10 who should be watched with care such as the patient having the possibility of falling from the bed or something. Accordingly, a proper response can be made with respect to the patient 10 who should be watched with care. Moreover, during nighttime in which a large number of patients are taken in charge by a small number of medical workers 1, it is possible to reduce the burden of service in the medical workers 11. In particular, at the time of dawn when a circadian rhythm (biological clock) of the medical worker 11 tends to be disturbed, attentiveness tends to be reduced and the medical worker 11 is apt to feel tired, therefore, it is difficult to pay careful attention to every patient 10. When adopting the above structure, it is possible to make a proper response to every patient 10 even at the time of dawn or the like. Furthermore, during a period in which there is not a notification of attention calling information, the medical worker 11 can watch the patients positively while reducing the degree of attention or tension, therefore, the burden of service in the medical worker 11 can be reduced.

As the patient identification information can be held in at least any of the measurement unit or the attention calling unit 60, the patient 10 as a target for the attention calling information can be positively specified.

<Operation Example 2>

An operation example of the medical service support method using the medical service support system 1 will be explained as an operation example 2. In the operation example 2, the same signs are given to operations overlapping those of the operation example 1 and explanation thereof is omitted.

In the operation example 2, S1 to S13 are performed in the same manner as the operation example 1. At this time, the emergency informing unit 30 measures and determines the state of the patient 10 independently of the determination of the determination by the attention calling unit 60. When a change requiring emergency treatment occurs such as a sudden change in the electrocardiogram occurring in the patient 10, the electrocardiograph 31 detects the change and determines that emergency treatment is necessary. The electrocardiograph 31 reports the determination result indicating requirement of emergency treatment to the display unit 72 through the communication unit 32. The medical worker 11 checks information indicating that emergency treatment is required informed from the electrocardiograph 31 by the display unit 72 and can hurry to the patient 10 requiring emergency treatment immediately.

According to the above configuration, the medical service support system 1 includes the medical service support device 20 and the emergency informing unit 30, determining the patient to whom attention should be paid easily based on the fact that the patient 10 is in the REM sleep state and moved in the given state and transmitting attention calling information, therefore, the medical worker 11 can specify the patient who should be watched with care among a large number of patients. Separately from the specification of the patient to be watched with care, when emergency treatment is necessary for the patient, the patient 10 can be positively specified and nursed in accordance with information from the emergency informing unit 30. That is, a proper response can be made in accordance with the state of the patient 10. Accordingly, a small number of medical workers 11 can watch a large number of patients positively and properly, which reduces the burden of service in the medical workers 11. In particular, during periods in which there is no notification by the emergency informing unit and no notification of attention calling information, the medical worker 11 can watch the patients positively while reducing the degree of attention or tension, therefore, the burden of service in the medical worker 11 can be reduced.

<Second Embodiment>

Next, a medical service support device and a medical service support method including a timer 90 which can set time such as a time instant or a time zone at which attention calling information is transmitted will be explained with reference to FIG. 1 to FIG. 3. The same signs are given to configurations and operations overlapping those in the first embodiment and explanation thereof is omitted.

The medical service support system 1 is configured to include the timer 90 which can set at least a start time when attention calling information is transmitted. The start time when attention calling information is transmitted can be, for example, a start time of a night shift. The time set by the timer 90 is not limited to the time instant at which attention calling information is transmitted. For example, it is possible to configure the system so as to set an end time at which transmission of attention calling information is ended, so as to set a time five hours or the like passing from the transmission start time and so as to set the transmission start time and the transmission end time.

The timer 90 is configured to perform communication with the attention calling unit 60 and to transmit the setting contents of the timer 90 to the attention calling unit 60. The communication between the timer 90 and the attention calling unit 60 can use a network such as the communication network L shown in FIG. 2 in which communication is performed in accordance with the general-purpose protocol in the same manner as communication between the attention calling unit 60 and the electrocardiogram sensor 40, the analysis unit 45 and the acceleration sensor 50.

The timer 90 is built in the display apparatus 70 shown in FIG. 1 as an example and is configured to set the start time and the end time at which attention calling information is transmitted. The display apparatus 70 is provided with a display unit 73 on which the setting contents of the timer 90 are displayed.

<Operation Example 3>

Next, as an operation example corresponding to the second embodiment, an operation example 3 of the medical service support method using the medical service support system 1 including the timer 90 will be explained with reference to FIG. 1 to FIG. 3. The same signs are given to configurations and operations overlapping those in the first embodiment and explanation thereof is omitted.

In the timer 90, the start time of the night shift is set as a start time at which attention calling information is transmitted and a start time of a day shift is set as an end time at which the transmission of attention calling information is ended.

The timer 90 transmits the start time and the end time at which attention calling information as the setting contents of the timer 90 is transmitted to the attention calling unit 60. The attention calling unit 60 received the setting contents of the timer 90 receives information from the analysis unit 45 and the acceleration sensor 50 before the start time at which attention calling information is transmitted, which does not make determination of the attention calling (S7), the attention (S8) and the light attention calling (S11) and does not transmit attention calling information (S7). Only the notification of emergency treatment by the emergency informing unit 30 is performed before the start time at which attention calling information is transmitted. It may also be preferable to adopt a structure in which only the transmission of attention calling information of S7 is not performed and the attention calling (S7), the attention (S8) and the light attention calling (S11) are determined before the start time of the timer 90 at which attention calling information is transmitted, then, the determination results are held in the attention calling unit 60. It may also be preferable to adopt a structure in which measurement by the electrocardiogram sensor 40 and detection by the acceleration sensor 50 are not performed before the start time of the timer 90 at which attention calling information is transmitted.

When the start time at which attention calling is transmitted comes, the attention calling unit 60 starts determination concerning whether the patient 10 as a measurement target should be watched with care or not based on the determination result received from the analysis unit 45 and the determination result received from the acceleration sensor 50 (S4 to S11 of FIG. 3), and starts transmission of attention calling information of S7. Specific operations of the attention calling unit 60 are the same as those of the operation example 1 and the operation example 2 according to the first embodiment, therefore, explanation is omitted.

When the end time at which transmission of attention calling information is ended comes, the attention calling unit 60 receives information from the analysis unit 45 and the acceleration sensor 50, but ends determination of the attention calling (S7), the attention (S8) and the light attention calling (S11) and ends the transmission of attention calling information (S7). After the end time at which attention calling information is transmitted set by the timer 90, only the notification of emergency treatment by the emergency informing unit 30 is performed.

According to the configuration, the timer 90 which can set the start time at which attention calling information is transmitted is provided, therefore, the transmission of attention calling information can be started so as to correspond to the time at which attention calling is necessary such as the start time of the night shift. Accordingly, even in a time zone in which a number of medical workers 11 is small, positive and proper response can be made in accordance with states of patients with respect to a large number of patients 10. Also according to the above configuration, the timer 90 which can set the end time at which attention calling information is transmitted, the transmission of attention calling information can be ended so as to correspond to a time zone in which a number of medical workers 11 is increased as end the night shift and start the day shift.

In the above embodiment, the example in which the electrocardiogram sensor 40, the analysis unit 45 and the acceleration sensor 50 are integrated into one apparatus and attached to the chest portion of the patient 10, and the attention calling unit 60 is attached to the chest portion close to the apparatus has been explained with reference to FIG. 1, however, configurations of the electrocardiogram sensor 40, the analysis unit 45, the acceleration sensor 50 and the attention calling unit 60 are not limited to the configurations shown in FIG. 1. For example, the electrocardiogram sensor 40, the analysis unit 45, the acceleration sensor 50 and the attention calling unit 60 may be configured as individual apparatuses as well as the electrocardiogram sensor 40, the analysis unit 45, the acceleration sensor 50 and the attention calling unit 60 may be integrated into one apparatus. It may also be preferable to adopt a structure in which the electrocardiogram sensor 40 and the acceleration sensor 50 are attached to the patient 10, the analysis unit 45 is built in an external apparatus which can be connected through the communication network L and the attention calling unit 60 is built in the bedside monitor 12 shown in FIG. 1. It may also be preferable to adopt a structure in which the electrocardiogram sensor 40 and acceleration sensor 50 are attached to the patient 10, and the analysis unit 45 and the attention calling unit 60 are built in the terminal apparatus 10A of the patient 10 shown in FIG. 1. It may also be further preferable to adopt a structure in which at least one of the analysis unit 45 and the attention calling unit 60 is provided in the apparatus such as the access point 80 shown in FIG. 1.

The measurement unit is not limited to the electrocardiogram sensor. Various types of sensors can be used as the measurement unit, which are capable of measuring biological information useful for specifying whether the patient 10 is a patient who should be watched with care or not among a large number of patients 10. As the measurement unit, a respiration sensor for measuring a respiration rate, a percutaneous arterial blood oxygen saturation sensor (hereinafter referred to as a "$SpO_2$ sensor") for measuring a value of percutaneous arterial blood oxygen saturation, a body temperature sensor for measuring a skin temperature (body temperature) and so on can be used instead of the electrocardiogram sensor 40 shown in FIG. 2. The number of sensors forming the measurement unit is not limited to one as shown in FIG. 2 but plural sensors can be used. Plural sensors included in the measurement unit may be at least one or more sensors of the electrocardiogram sensor 40, the respiration sensor, the $SpO_2$ sensor and the body temperature sensor.

According to the above structure, biological information of the patient is measured by using at least one or more of the electrocardiogram sensor, the $SpO_2$ sensor, the respiration sensor and the body temperature sensor concerning the sleep state of the patient 10, therefore, the sleep state can be measured with a simple method without using a large-scaled device as compared with the determination of the sleep state by an electroencephalograph using multi-channel electrodes or by measuring brain waves using a paste for reducing noise, which can reduce the burden of the patient 10 concerning the determination of the sleep state. Furthermore, in the case where biological information of the patient is measured by using one or more sensors, the determination of the sleep state can be performed more accurately and the accuracy of determination concerning whether attention calling (alert) is necessary or not can be improved more as compared with the case of using one sensor.

Analysis by the analysis unit is not limited to the above analysis of electrocardiogram data. The analysis unit may have various configurations capable of analyzing whether the patient 10 is in the REM sleep state or in the Non-REM sleep state based on the measurement result by the measurement unit for determining whether the patient 10 is the patient to be watched with care among a large number of patients 10. For example, in the medical service support device 20 including the skin temperature (body temperature) sensor as the measurement unit, the analysis unit may have a structure in which variations in body temperature concerning whether the body temperature is reduced or not are analyzed based on the measurement result (body temperature data) acquired from the body temperature sensor to determine whether the patient 10 is in the REM sleep state or in the Non-REM sleep state.

<Modification Example: Medical Service Support Device 20A>

An example of a medical service support device 20A including a respiration sensor 41 instead of the electrocardiogram sensor 40 as the measurement unit will be explained with reference to FIG. 4. The same signs are given in FIG. 4 to the same configurations as those of the medical service support device 20 shown in FIG. 1 to FIG. 3 and explanation thereof is omitted.

Figure 4:
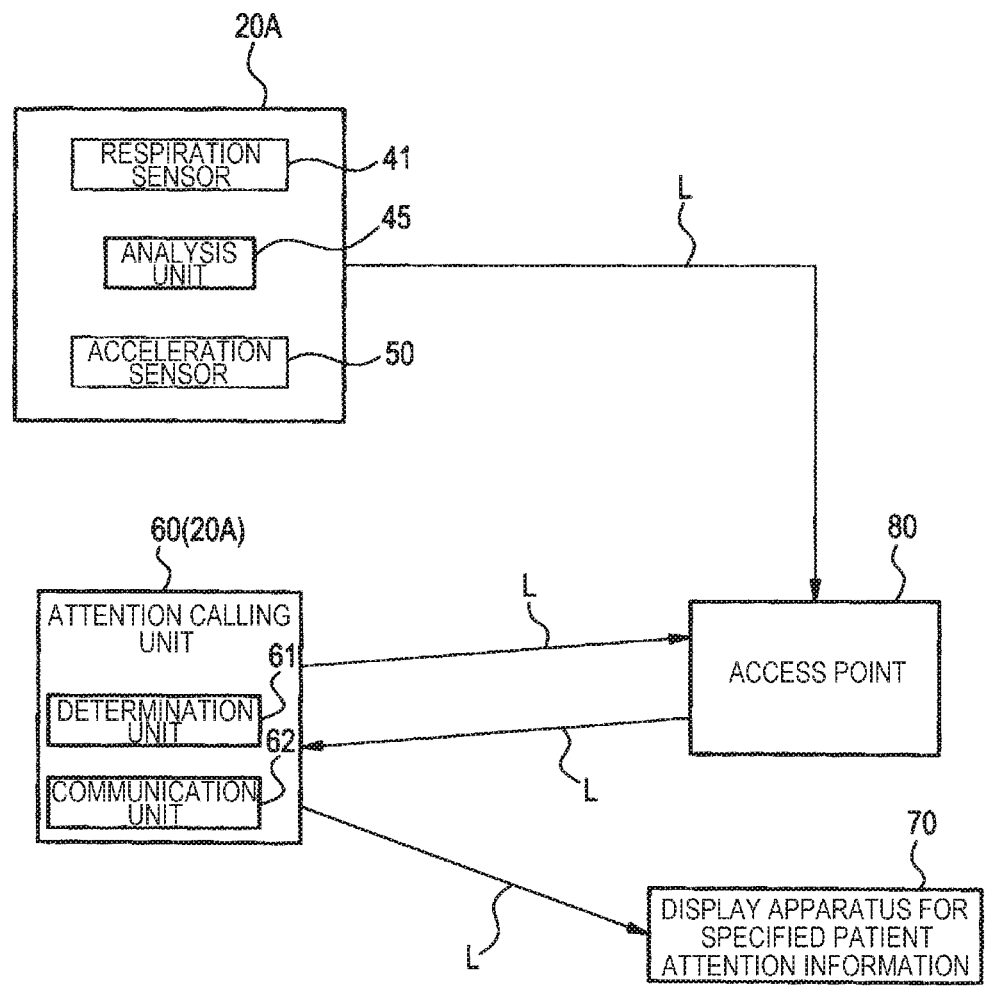
FIG. 4 is a function block diagram showing an outline of a modification example of the medical service support device.

The medical service support device 20A includes the respiration sensor 41, the analysis unit 45, the acceleration sensor 50, the attention calling unit 60 as shown in FIG. 4.

The respiration sensor 41 is a sensor attached to one of nostrils of the patient 10 and measuring the respiration rate of the patient 10. The respiration sensor 41 is configured to transmit the measurement result of the respiration rate of the patient 10 to the analysis unit 45. The analysis unit 45 analyzes variations in respiration concerning whether the respiration is regular or not, whether a respiratory frequency is low or not and so on based on the measurement result (data of the respiration rate and so on) acquired from the respiration sensor 41 to determine whether the patient 10 is in the REM sleep state or in the Non-REM sleep.

The operation example of a medical service support method using the medical service support device 20A is common to the operation example 1 to the operation example 3 of the medical service support method using the medical service support device 20 except that the measurement by the electrocardiogram sensor 40 is changed to the measurement by the respiration sensor 41 and that the electrocardiogram data is changed to the measurement result by the respiration sensor 51 such as the respiration rate, therefore, explanation is omitted.

As described above, according to the medical service support device 20A including the respiration sensor 41 and the medical service support method using the medical service support device 20A, it is possible to determine that the patient is in the REM sleep state with a simple method. Additionally, the attention calling unit 60 can transmit attention calling information by easily determining the patient to be watched with care by combining the sleep state of the patient 10 with the determination of a motion indicating that the patient moves in the given state, therefore, the medical worker 11 can specify the patient 10 who should be watched with care having a possibility of, for example, falling from the bed or the like among a large number of patients 10. Accordingly, proper response can be made with respect to the patient 10 who should be watched with care. It is also possible to reduce the burden of services in the medical worker 11 during nighttime in which a large number of patients are taken in charge by a small number of medical workers 11.

Figure 3:
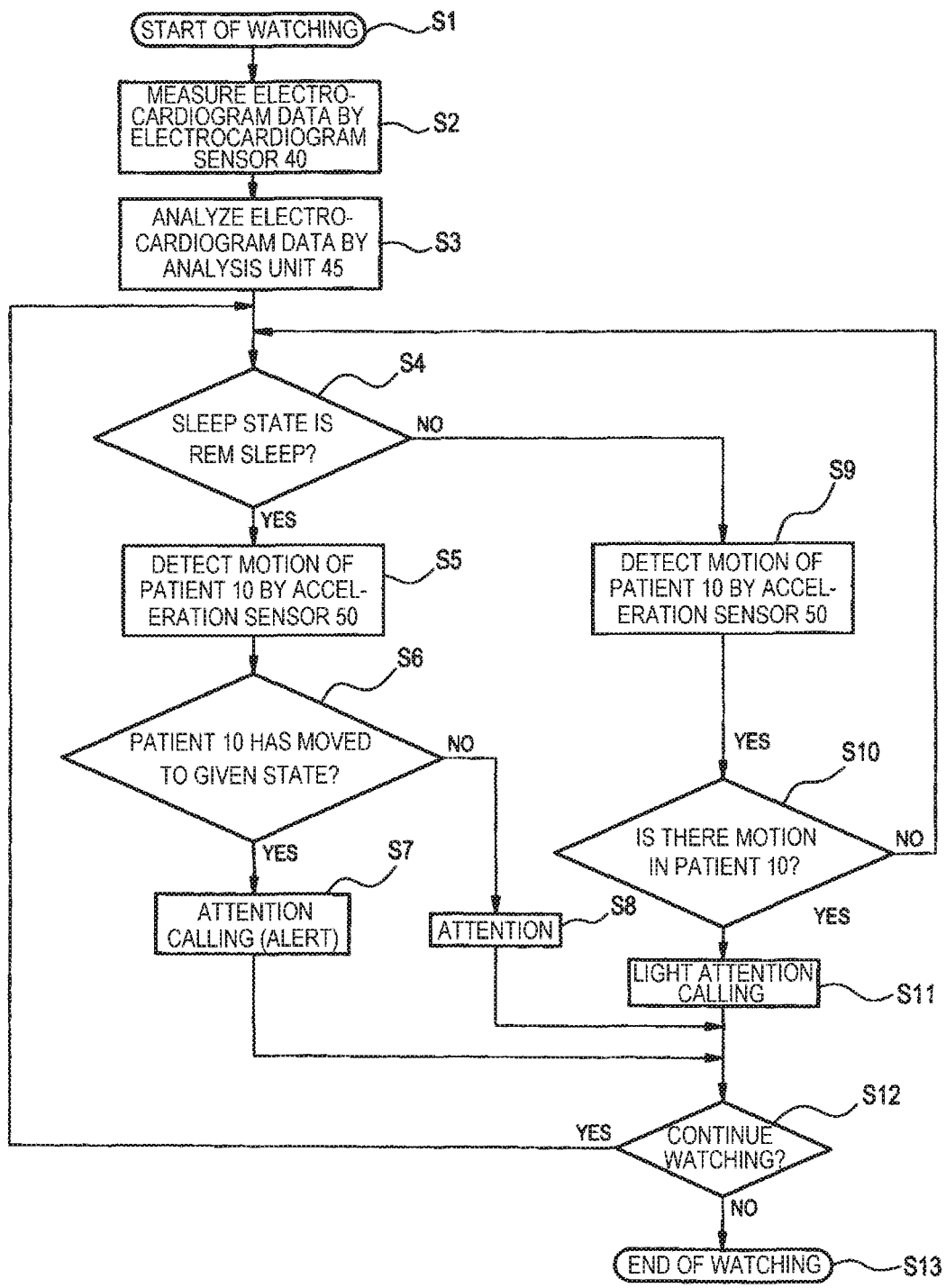
FIG. 3 is a flowchart showing an operation example of the medical service support device and a medical service support method according to the embodiment of the present disclosure.

In the above embodiment, the example in which attention calling information is transmitted to an external portion of the medical service support devices 20 and 20A in the case of S7 of FIG. 3 where the patient is determined to be in the REM sleep state and moved in the given state has been explained, however, the transmission to the external portion of the devices is not limited to the above example. For example, it is also possible to create information corresponding to the attention (S8) and the light attention calling (S11) as determination results in the attention calling unit and to transmit the information to the external portion also in S8 (attention) and S11 (light attention calling) in FIG. 3.

Furthermore, the example in which attention calling information is displayed on the display unit 71 has been explained in the above embodiment, however, the display on the display unit 71 is not limited to the above. For example, the display unit 71 may display information indicating that light attention calling is necessary and the patient identification number of the patient 10 requiring the light attention calling, and may display information indicating that attention is necessary and the patient identification number of the patient 10 requiring the attention. The medial worker 11 can check the light attention calling, attention and the patient identification number displayed on the display unit 71 and can watch the patient 10 properly so that the patient 10 does not fall from the bed or the like.

The present disclosure is not limited to the above embodiments and operation examples, and modifications, improvements and so on may occur appropriately. Additionally, the material, the shape, the state, the number, the arrangement place and so on of respective components in the above embodiments are arbitrary and not limited as long as the present disclosure is achieved.

What is claimed is:

1. A medical service support device comprising:
    a measurement unit attached to a patient and including at least one sensor that is configured to measure biological information of the patient;
    an analysis unit configured to analyze the biological information;
    a detection unit configured to detect a motion of the patient; and
    an attention calling unit configured to transmit attention calling information and patient identification information for specifying the patient toward the external portion of the device when it is determined that the patient is in a REM sleep state based on an analysis result by the analysis unit as well as determined that the patient has moved to a given state based on a detection result by the detection unit, wherein the given state indicates the motion exceeds a change amount, the change amount based on a dimension of the patient's bed and a dimension of the patient.

2. The medical service support device according to claim 1,
    wherein the sensor is at least one or more of an electrocardiogram sensor, a percutaneous arterial blood oxygen saturation sensor, a respiration sensor and a body temperature sensor.

3. The medical service support device according to claim 1,
    wherein the patient identification information is held in at least one of the measurement unit and the attention calling unit.

4. The medical service support device according to claim 1, further comprising:
    a timer configured to perform communication with the attention calling unit and configured to set at least a start time at which the attention calling information is configured to be transmitted.

5. A medical service support system comprising:
    a medical service support device according to claim 1; and
    an emergency informing unit configured to inform the contents of emergency treatment by detecting that the emergency treatment is necessary for the patient.

6. The medical service support device according to claim 1,
    wherein the given state indicates the patient is in imminent danger.

7. A medical service support method comprising the steps of:
    measuring biological information of a patient;
    analyzing the biological information;
    determining whether the patient is in a REM sleep state or not based on an analysis result in the step of analysis;
    detecting a motion of the patient by a detection unit;
    determining whether the motion of the patient detected by the detection unit is movement to a given state or not; and
    transmitting attention calling information and patient identification information for specifying the patient to the an external portion when it is determined that the patient is in the REM sleep state as well as determined that the patient has moved to the given state, wherein the given state indicates the motion exceeds a change amount, the change amount based on a dimension of the patient's bed and a dimension of the patient.

8. The medical service support method according to claim 7, wherein the given state indicates the patient is in imminent danger.

\* \* \* \* \*